(12) United States Patent
Brueck et al.

(10) Patent No.: US 10,976,299 B1
(45) Date of Patent: *Apr. 13, 2021

(54) FABRICATION OF ENCLOSED NANOCHANNELS USING SILICA NANOPARTICLES

(71) Applicant: UNM RAINFOREST INNOVATIONS, Albuquerque, NM (US)

(72) Inventors: Steven R. J. Brueck, Albuquerque, NM (US); Yuliya Kuznetsova, Albuquerque, NM (US); Alexander Neumann, Albuquerque, NM (US)

(73) Assignee: UNM RAINFOREST INNOVATIONS, Albuquerque, NM (US)

( * ) Notice: Subject to any disclaimer, the term of this patent is extended or adjusted under 35 U.S.C. 154(b) by 266 days.

This patent is subject to a terminal disclaimer.

(21) Appl. No.: 15/944,226

(22) Filed: Apr. 3, 2018

Related U.S. Application Data

(60) Division of application No. 14/868,128, filed on Sep. 28, 2015, now Pat. No. 10,060,904, which is a (Continued)

(51) Int. Cl.
*B01D 69/04* (2006.01)
*B81C 1/00* (2006.01)
(Continued)

(52) U.S. Cl.
CPC ... *G01N 33/48721* (2013.01); *B81C 1/00071* (2013.01); *C12Q 1/6869* (2013.01);
(Continued)

(58) Field of Classification Search
CPC ............ G01N 27/447; G01N 33/48721; B81C 1/00071; B81C 2201/0159; C12Q 1/6869;
(Continued)

(56) References Cited

U.S. PATENT DOCUMENTS

| 3,977,967 A | 8/1976 | Trulson et al. |
| 5,234,594 A | 8/1993 | Tonucci et al. |

(Continued)

FOREIGN PATENT DOCUMENTS

| CA | 2 931 784 | * | 6/2015 | ................ B01L 7/00 |
| WO | WO2015/081294 A8 | | 6/2015 | |

*Primary Examiner* — Mary A Wilczewski
(74) *Attorney, Agent, or Firm* — MH2 Technology Law Group LLP

(57) ABSTRACT

In accordance with the disclosure, a method of forming a nanochannel is provided. The method includes depositing a photosensitive film stack over a substrate; forming a pattern on the film stack using interferometric lithography; depositing a plurality of silica nanoparticles to form a structure over the pattern; removing the pattern while retaining the structure formed by the plurality of silica nanoparticles, wherein the structure comprises one or more enclosed nanochannels, wherein each of the one or more nanochannels comprise one or more sidewalls and a roof; and partially sealing the roof of one or more nanochannels, wherein the roof comprises no more than one unsealed nanochannel per squared micron.

12 Claims, 10 Drawing Sheets

Related U.S. Application Data continuation-in-part of application No. 13/831,537, filed on Mar. 14, 2013, now Pat. No. 9,156,004, which is a continuation-in-part of application No. 12/892,427, filed on Sep. 28, 2010, now Pat. No. 8,404,123, which is a division of application No. 11/549,732, filed on Oct. 16, 2006, now Pat. No. 7,825,037.

(60) Provisional application No. 60/726,651, filed on Oct. 17, 2005.

(51) Int. Cl.
  *G01N 33/487* (2006.01)
  *G03F 7/20* (2006.01)
  *C12Q 1/6869* (2018.01)
  *G01N 27/447* (2006.01)

(52) U.S. Cl.
  CPC ......... *G01N 27/447* (2013.01); *G03F 7/2051* (2013.01); *B81C 2201/0159* (2013.01)

(58) Field of Classification Search
  CPC ....... G03F 7/2051; B01D 69/04; B82Y 30/00; Y10T 137/0324; Y10T 137/3006; Y10S 977/78; Y10S 977/84
  See application file for complete search history.

(56) References Cited

U.S. PATENT DOCUMENTS

| | | |
|---|---|---|
| 5,750,415 A | 5/1998 | Gnade et al. |
| 5,801,092 A | 9/1998 | Ayers |
| 5,843,767 A | 12/1998 | Beattie |
| 5,952,665 A | 9/1999 | Bhargava |
| 6,074,893 A | 6/2000 | Nakata et al. |
| 6,129,901 A | 10/2000 | Moskovits et al. |
| 6,136,212 A | 10/2000 | Mastrangelo et al. |
| 6,231,744 B1 | 5/2001 | Ying et al. |
| 6,287,987 B1 | 9/2001 | Miller et al. |
| 6,300,640 B1 | 10/2001 | Bhargava et al. |
| 6,331,479 B1 | 12/2001 | Li et al. |
| 6,359,288 B1 | 3/2002 | Ying et al. |
| 6,452,184 B1 | 9/2002 | Taskar et al. |
| 6,610,593 B2 | 8/2003 | Kohl et al. |
| 6,616,821 B2 | 9/2003 | Broadley et al. |
| 6,685,810 B2 | 2/2004 | Noca et al. |
| 6,763,585 B2 | 7/2004 | Suzuki |
| 6,913,697 B2 | 7/2005 | Lopez et al. |
| 7,052,821 B2 | 5/2006 | Kohl et al. |
| 7,122,153 B2 | 10/2006 | Ho |
| 7,166,531 B1 | 1/2007 | van den Hoek et al. |
| 7,290,667 B1 | 11/2007 | Bakajin et al. |
| 7,335,395 B2 | 2/2008 | Ward et al. |
| 7,435,488 B2 | 10/2008 | Tomita et al. |
| 7,470,954 B2 | 12/2008 | Lee et al. |
| 7,476,501 B2 | 1/2009 | Chan et al. |
| 7,510,982 B1 | 3/2009 | Draeger et al. |
| 7,525,037 B2 | 4/2009 | Hansson et al. |
| 7,612,358 B2 | 11/2009 | Joo et al. |
| 7,629,224 B1 | 12/2009 | van den Hoeck et al. |
| 7,641,863 B2 | 1/2010 | Doktycz et al. |
| 7,682,591 B2 | 3/2010 | Black et al. |
| 7,704,608 B2 | 4/2010 | Thies et al. |
| 7,745,101 B2 | 6/2010 | Tutt et al. |
| 7,790,234 B2 | 9/2010 | Ayers |
| 7,825,037 B2 | 11/2010 | Brueck et al. |
| 7,833,355 B2 | 11/2010 | Capizzo |
| 7,842,352 B2 | 11/2010 | Gemici et al. |
| 7,875,315 B2 | 1/2011 | Ayers |
| 7,883,742 B2 | 2/2011 | Ayers |
| 7,919,188 B2 | 4/2011 | Ayers |
| 7,955,614 B2 | 6/2011 | Martin et al. |
| 7,985,385 B2 | 7/2011 | Lincoln |
| 7,993,524 B2 | 8/2011 | Ratto et al. |
| 8,105,471 B1 | 1/2012 | Han et al. |
| 8,158,409 B2 | 4/2012 | Wei et al. |
| 8,163,154 B1 | 4/2012 | Hatch et al. |
| 8,293,193 B2 | 10/2012 | Ricoul et al. |
| 8,297,449 B2 | 10/2012 | Afzali-Ardakani et al. |
| 8,329,115 B2 | 12/2012 | Han et al. |
| 8,404,123 B2 | 3/2013 | Brueck et al. |
| 8,514,398 B2 | 8/2013 | Pang et al. |
| 8,722,327 B2* | 5/2014 | Cao .................. G01N 21/6428 435/6.1 |
| 8,940,173 B2 | 1/2015 | Bakajin et al. |
| 9,156,004 B2 | 10/2015 | Brueck et al. |
| 9,927,397 B1* | 3/2018 | Brueck ............ G01N 33/48721 |
| 10,184,930 B2* | 1/2019 | Brueck ............ B01L 3/502761 |
| 2002/0072243 A1 | 6/2002 | Craighead et al. |
| 2004/0005258 A1 | 1/2004 | Fonash et al. |
| 2004/0132218 A1 | 7/2004 | Ho |
| 2004/0149568 A1 | 8/2004 | Huang et al. |
| 2005/0170670 A1 | 8/2005 | King et al. |
| 2005/0191774 A1 | 9/2005 | Li et al. |
| 2005/0196779 A1 | 9/2005 | Ho et al. |
| 2006/0015061 A1 | 1/2006 | Kuo et al. |
| 2006/0175653 A1 | 8/2006 | Joo et al. |
| 2006/0274230 A1 | 12/2006 | Shao et al. |
| 2006/0278580 A1 | 12/2006 | Striemer et al. |
| 2007/0122313 A1* | 5/2007 | Li ......................... B82Y 30/00 422/400 |
| 2007/0134939 A1 | 6/2007 | Brueck et al. |
| 2007/0264481 A1 | 11/2007 | Desimone et al. |
| 2008/0242556 A1 | 10/2008 | Cao et al. |
| 2008/0251382 A1 | 10/2008 | Han et al. |
| 2009/0214392 A1 | 8/2009 | Kameoka et al. |
| 2009/0224435 A1 | 9/2009 | Gogotsi et al. |
| 2009/0243428 A1 | 10/2009 | Qiao |
| 2009/0305278 A1 | 12/2009 | Hardin et al. |
| 2010/0104650 A1 | 4/2010 | Lee et al. |
| 2010/0301462 A1 | 12/2010 | Sinha et al. |
| 2011/0011794 A1 | 1/2011 | Brueck et al. |
| 2011/0168560 A1 | 7/2011 | Afzali-Ardakani et al. |
| 2012/0105853 A1 | 5/2012 | Pang et al. |
| 2013/0193065 A1 | 8/2013 | Brueck et al. |
| 2014/0204372 A1 | 7/2014 | Pang et al. |
| 2016/0377590 A1 | 12/2016 | Brueck et al. |
| 2017/0299548 A1 | 10/2017 | Yoshida et al. |
| 2019/0227050 A1* | 7/2019 | Brueck ............ G01N 33/48721 |

* cited by examiner

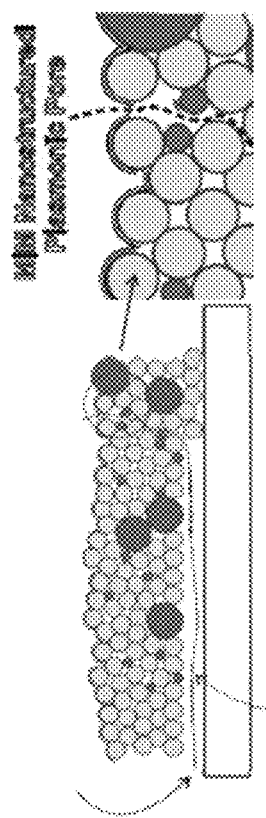

FABRICATION OF ENCLOSED NANOCHANNELS USING SILICA NANOPARTICLES

CROSS REFERENCE TO RELATED APPLICATION

This application is a divisional of U.S. patent application Ser. No. 14/868,128 filed Sep. 28, 2015 (now allowed), which is a continuation-in-part application of U.S. patent application Ser. No. 13/831,537 filed on Mar. 14, 2013, which is a continuation-in-part application of U.S. patent application Ser. No. 12/892,427 filed on Sep. 28, 2010, now U.S. Pat. No. 8,404,123 issued on Mar. 26, 2013, which is a divisional application of U.S. patent application Ser. No. 11/549,732 filed on Oct. 16, 2006, now U.S. Pat. No. 7,825,037 issued on Nov. 2, 2010, which claims priority to U.S. Provisional Patent Application Ser. No. 60/726,651 filed on Oct. 17, 2005, the disclosures of which are incorporated by reference herein in their entirety.

GOVERNMENT INTEREST

This invention was made with U.S. Government support under Grant No. DAAD19-99-1-0196 awarded by the Army Research Office and Grant No. HR0011-05-1-0006 awarded by the DOD/Defense Advanced Research Projects Agency. The U.S. Government has certain rights in the invention.

FIELD OF THE INVENTION

The subject matter of this invention relates to fabrication of micro/nano structures. More particularly, the subject matter of this invention relates to nanochannels and a method for fabricating enclosed nanochannels using lithography and self assembly of silica nanoparticles.

BACKGROUND OF THE INVENTION

Micro and nano structures including nanoparticle assembly with two and three dimensional periodicity can have potential applications in the areas of photonic crystals, chemical sensors, catalysts, and biotechnology. Patterned surfaces can be used as hard templates to assist the self assembly of not only relatively simple clusters but also complex and unique crystallization structures. Soft polymer templates have been used for directed self assembly of particle arrays on flat substrates. Binary colloidal crystals have been fabricated using two different sizes of colloidal particles. Further, micro and nano particles have been used as templates for the preparation of porous metallic nanostructures and monodisperse colloidal crystals. Even though nanochannel structures for nanofluidic applications have been fabricated using thermal oxidation or nanoimprint, there is a need for a simple and inexpensive approach for the fabrication of enclosed channels formed of nanoparticles.

Thus, there is need to solve these and other problems of the prior art and provide a simple method for the fabrication of nanochannel structures.

SUMMARY OF THE INVENTION

In accordance with the teachings of the present invention, there is a method of forming a nanochannel including depositing a photosensitive film stack over a substrate and forming a pattern on the film stack using interferometric lithography. The method can further include depositing a plurality of silica nanoparticles to form a structure over the pattern and removing the pattern while retaining the structure formed by the plurality of silica nanoparticles, wherein the structure includes an enclosed nanochannel.

According to various embodiments, there is a method of forming a multilayer silica nanochannel structure including forming a first layer of silica nanochannels. The step of forming the first layer of silica nanochannels having a first spatial period and a first aspect ratio includes: (a) depositing a film stack over a substrate; (b) forming a pattern on the film stack using lithography; (c) depositing a plurality of silica nanoparticles to form a structure over the pattern; and (d) removing the pattern while retaining the structure formed by the plurality of silica nanoparticles, wherein the structure comprises enclosed silica nanochannels. The method of forming multilayer silica nanochannel can also include forming a second layer of silica nanochannel having a second spatial period and a second aspect ratio over the first layer of silica nanochannels by repeating steps a-d to form the second layer of silica nanochannels and repeating steps a-d m−2 times to form an m layered silica nanochannel structure.

According to various embodiments, there is another method of forming a multilayer silica nanochannel structure including forming a first layer of silica nanochannels having a first spatial period and a first aspect ratio. The step of forming first layer of silica nanochannels includes (a) depositing a film stack over a substrate; (b) forming a pattern on the film stack using lithography; (c) depositing a plurality of silica nanoparticles to form a structure over the pattern. The method of forming a multilayer silica nanochannel structure can further include repeating the steps a-c to form a second layer of structure having a second spatial period and a second aspect ratio over the first layer of structure. The method can further include repeating the steps a-c (m−2) times to get m layers of structure over m layers of pattern and removing the m layers of pattern while retaining the structure formed by the plurality of silica nanoparticles, thereby forming m layers of silica nanochannel structure.

According to various embodiments there is a nanochannel device for selectively separating components of a fluid including at least one first nanochannel having a first opening, at least one second nanochannel with a second opening, wherein the first opening is in a direction different from the first opening, and at least one more porous sidewall having a plurality of pores between the first and the second nanochannel, wherein the first nanochannel, the second nanochannel, and the at least one porous sidewall are disposed such that the fluid enters through the first opening of the first nanochannel, percolates through the plurality of pores of the porous sidewall and exits through the second opening of the second nanochannel.

According to various embodiments, there is a method of diagnosing nanochannel formation. The method can include depositing a drop of a suspension including silica nanoparticles on a patterned surface, determining that a nanochannel is not completely formed if the suspension of silica nanoparticles forms an elongated drop along a direction of the pattern, and determining that a top of the nanochannel is formed if the suspension of silica nanoparticles shows wetting.

In implementations, a method of forming a nanochannel is disclosed. The method can include depositing a photosensitive film stack over a substrate; forming a first pattern on the film stack using interferometric lithography to form a nanochannel; forming a second pattern on the film stack using interferometric lithography and a mask aligner to form a barrier in the nanochannel; depositing a plurality of silica nanoparticles to form a structure over the pattern; and removing the first pattern and the second pattern while retaining the structure formed by the plurality of silica nanoparticles, wherein the structure comprises an enclosed nanochannel with the barrier formed along a portion of the enclosed nanochannel.

In implementations, the depositing a photosensitive film stack can comprise depositing a first layer comprising an antireflective coating over the substrate and depositing a second layer comprising a photoresist over the first layer.

In implementations, the second layer can comprise a layer of positive photoresist or a layer of negative photoresist.

In implementations, the depositing the plurality of silica nanoparticles can comprise at least one cycle of spin coating using a suspension of silica nanoparticles.

In implementations, the depositing the plurality of silica nanoparticles can comprise multiple cycles of spin coating wherein each cycle of spin coating uses a suspension of silica nanoparticles with a same size distribution.

In implementations, the depositing the plurality of silica nanoparticles can comprise multiple cycles of spin coating wherein at least one cycle of spin coating uses a suspension of silica nanoparticles with a size distribution different than the other cycles of spin coating.

In implementations, a nanochannel device for selectively separating components of a fluid is disclosed. The nanochannel device can comprise at least one first nanochannel comprising a first opening, a second opening, and a barrier positioned between the first opening and the second opening, wherein the barrier comprises a plurality of pores to allow fluid to flow from the first opening to the second opening.

In implementations, the nanochannel device can further comprise a second nanochannel arranged perpendicular to the first nanochannel and separated from the first nanochannel by a barrier comprised of a plurality of pores to allow fluid to flow from the first nanochannel to the second nanochannel.

In implementations, the second nanochannel can comprise a first opening, a second opening, and a barrier positioned between the first opening and the second opening, wherein the barrier comprising a plurality of pores to allow fluid to flow from the first opening to the second opening wherein a thickness and/or a pore size, controlled by the nanoparticle size, of the barrier between the first opening and the second opening is adjusted relative to the thickness and or the pore size, controlled by the nanoparticle size, of the barrier between the first and the second nanochannel to affect the flow of moieties across the two barriers.

In implementations, the nanochannel device can comprise at least one porous divider arranged between the first and the second nanochannel.

In implementations, the at least one porous divider can comprise a plurality of pores between the first and the second nanochannel, wherein the first nanochannel, the second nanochannel, and the at least one porous divider are disposed such that the fluid enters through the first opening of the first nanochannel, percolates through the plurality of pores of the porous divider and exits through the second opening of the second nanochannel.

In implementations, the nanochannel device can further comprise functionalized silica nanoparticles to selectively transport one component of the fluid.

In implementations, the nanochannel device can further comprise a CVD film providing sealing of the top surface of the roof of the nanochannels.

In implementations, the CVD film can be composed of $SiO_2$ and $Si_3N_4$.

In implementations, the nanochannel device can further comprise an atomic layer deposited film atop the chemical vapor deposited film, where the atomic layer deposited film can be $Al_2O_3$.

In implementations, a method of forming a nanochannel is provided. The method can comprise depositing a photosensitive film stack over a substrate; forming a pattern on the film stack using interferometric lithography; depositing a plurality of silica nanoparticles to form a structure over the pattern; removing the pattern while retaining the structure formed by the plurality of silica nanoparticles, wherein the structure comprises one or more enclosed nanochannels, wherein each of the one or more nanochannels comprise one or more sidewalls and a roof; and partially sealing the roof of one or more nanochannels, wherein the roof comprises no more than one unsealed nanochannel per squared micron.

In implementations, the one or more enclosed nanochannels are self-assembled formed by directed spin-coating of the plurality of silica nanoparticles.

In implementations, the one or more nanochannels have a period of about 1 µm and a linewidth of about 10 nm to about 100 nm.

In implementations, the nanoparticles that form the roof, walls and barriers form tortuous nanopores that slow the translocation speed of the target molecule.

In implementations, the plurality of silica nanoparticles are deposited in a quasi-hexagonal-close-packed geometry.

In implementations, the method can further comprise spin-coating the plurality of silica nanopartices, removing remaining hydrocarbon film, and calcining the structure.

In implementations, the method can further comprise forming one or more additional nanochannels arranged in either parallel or perpendicular nanochannel directions.

In implementations, the partially sealing is performed by an atomic layer deposition process, a chemical vapor deposition, or a combination thereof.

In implementations, the partially sealing comprises sealing some of the externally accessible pores between a plurality of nanoparticles that form the roof.

In implementations, a method for a manipulating a target molecule is provided. The method can comprise providing a nanochannel having a partially sealed porous roof comprising a plurality of exposed unsealed pores and a plurality of tortuous nanopores; introducing a sample comprising the target molecule to the nanochannel; and allowing the target molecule to travel through the unsealed tortuous nanopores in the partially sealed porous roof before or after the target molecule travels through the nanochannel.

In implementations, the sample is introduced to the nanochannel by placing the sample on the roof, thus forcing the target molecule to travel through the tortuous nanopores prior to traveling through the nanochannel.

In implementations, the target molecule exits the nanochannel through the roof, thus forcing the target molecule to travel through the tortuous nanopores after traveling through the nanochannel.

In implementations, a nanochannel device for manipulating a target long chain molecule is provided. The device can comprise a first plurality of nanochannels, wherein each nanochannel comprises a first opening and a second opening of the first plurality of nanochannels; a second plurality of nanochannels, wherein each nanochannel comprises a first opening and a second opening of the second plurality of nanochannels; and a barrier positioned between the first plurality of nanochannels and the second plurality of nanochannels, wherein the barrier comprises a plurality of silica nanoparticles, wherein the barrier allows the target long chain molecule to accumulate.

In implementations, the second plurality of nanochannels are arranged perpendicular to the first plurality of nanochannels and separated from the first plurality of nanochannels by the barrier.

In implementations, a thickness and/or a pore size of the barrier is controlled by a size of the nanoparticle to affect a flow of moieties across the barrier.

In implementations, the device can comprise at least one porous divider arranged between the first and the second plurality of nanochannels.

In implementations, the device can comprise functionalized silica nanoparticles to selectively control the translocation speed through the tortuous nanopore of the target long chain molecule.

In implementations, a method for forming a device for the manipulation of a target molecule is provided. The method can comprise providing a nanochannel having a common porous roof comprising a plurality of tortuous nanopores; sealing some of the nanopores in the porous roof via conformal atomic layer deposition (ALD); and partially sealing others of the nanopores by the same conformal ALD process.

In implementations, the method can further comprise forming a layer over the roof via chemical vapor deposition (CVD).

In implementations, the size of at least one of the unsealed pores enables translocation of single molecule one at a time.

Additional advantages of the embodiments will be set forth in part in the description which follows, and in part will be obvious from the description, or may be learned by practice of the invention. The advantages will be realized and attained by means of the elements and combinations particularly pointed out in the appended claims.

It is to be understood that both the foregoing general description and the following detailed description are exemplary and explanatory only and are not restrictive of the invention, as claimed.

The accompanying drawings, which are incorporated in and constitute a part of this specification, illustrate embodiments of the invention and together with the description, serve to explain the principles of the invention.

BRIEF DESCRIPTION OF THE DRAWINGS

FIGS. 10A-10B depict of an exemplary method of DNA manipulation according to an embodiment of the disclosure

DESCRIPTION OF THE EMBODIMENTS

Figure 1A:
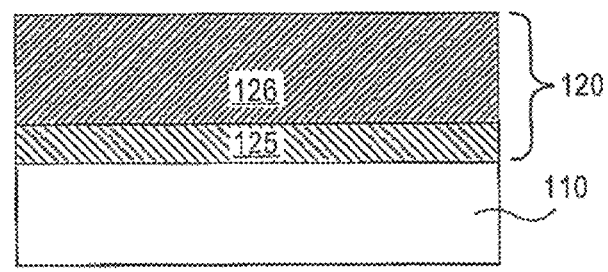
FIGS. 1A to 1E illustrate an exemplary method of forming nanochannels using silica nanoparticles in accordance with various embodiments of the present teachings.

Reference will now be made in detail to the present embodiments, examples of which are illustrated in the accompanying drawings. Wherever possible, the same reference numbers will be used throughout the drawings to refer to the same or like parts.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein. For example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 5. In certain cases, the numerical values as stated for the parameter can take on negative values. In this case, the example value of range stated as "less that 10" can assume negative values, e.g. −1, −2, −3, −10, −20, −30, etc.

In some embodiments, the present disclosure provides methods and apparatus for long read, label-free, optical nanopore long chain molecular recognition mapping. In general, the present disclosure describes a novel molecular recognition mapping technology based on the integration of nanochannels to deliver single long-chain molecules with widely spaced (>wavelength), ~1-nm aperture "tortuous" nanopores that slow translocation sufficiently to provide massively parallel, single base resolution using optical techniques. A novel, directed self-assembly nanofabrication scheme using simple colloidal nanoparticles is used to form the nanopore arrays atop nanochannels that unfold the long chain molecules. At the surface of the nanoparticle array, strongly localized electromagnetic fields in engineered plasmonic/polaritonic structures allow for single moiety resolution using optical techniques. Surface Enhanced Coherent Anti-Stokes Raman Spectroscopy (SECARS) is one such technique that has the advantage of not requiring labeling of the bases. Fluorescence techniques with labeled bases provide an alternative possibility.

According to a first embodiment, the present disclosure provides a nanochannel including a system of tortuous nanopores having a partially sealed porous roof. According to another embodiment, the nanochannel further comprises an integrated metal-insulator-metal (MIM) plasmonic or polaritonic structure that enhances optical detection and provides the necessary spatial localization for single molecule readouts. According to yet another embodiment the present disclosure provides methods and apparatus for long read, label-free, optical nanopore molecular or long chain molecular recognition mapping. Suitable long chain molecules (sometimes referred to herein as "molecules" or "molecules of interest") include DNA, RNA, proteins, etc. Of course it will be understood that while various embodiments and examples may make reference to a specific type of long chain molecule, such as DNA, unless otherwise specifically stated, the present disclosure contemplates that such embodiments and examples are similarly applicable to other types of long-chain molecules including, but not necessarily limited to RNA and proteins.

According to some embodiments, the sequencing technology described herein may be capable of sequencing a full human. According to various embodiments, the technology described herein make use of one or more of: an integrated system of nanochannels; tortuous (extended and convoluted) nanopores at a separation greater than an optical wavelength; a metal-insulator-metal (MIM) plasmonic or polaritonic structure, or other optical detection enhancement structure as described herein; and an optical readout mechanism such as surface-enhanced coherent anti-Stokes Raman scattering or labeled fluorescence techniques.

According to still further embodiments, the present disclosure provides methods for making each of the above. According to some embodiments, only a single, straightforward lithography step, at an easily accessed pitch of ~1 μm is required. According to various embodiments, nanoscale features are produced by directed self-assembly processes making this an inexpensive and field-replaceable technology.

According to various embodiments, the present disclosure utilizes nanochannels formed from nanoparticles. According to an embodiment, self-assembled nanochannels can be formed by directed spin-coating of nanoparticles (~50 nm diameter or less) onto photoresist walls, formed by a sequence of lithography steps that include some appropriate variant of exposure, development and etching as is well known in the art, such that the nanoparticles are "stacked up" to form the nanochannel walls and roofs. Suitable materials for forming the nanoparticles include materials for which a method to selectively remove the photoresist exists. Furthermore, it will be understood that in those embodiments wherein the nanochannel is to be used with nucleic acids, the material should be hydrophillic to enable filling of the nanopores with a solution and negatively charged to enable transloction of the nucleic acids through the nanopores. According to a specific embodiment, silica nanoparticles have been found to meet all of the above-identified requirements. The spin-coating step is followed by a "lost-wax" calcination step that burns out the photoresist, sinters the nanoparticles to provide mechanical strength, and provides a hydrophilic surface for fluid introduction. Alternate processes such as solvent removal can be used to remove the photoresist and the ARC layers. Additional details for the formation of such nanochannels can be found in U.S. Pat. No. 7,825,037, which is hereby incorporated by reference.

In other applications, such as sequencing of some proteins, a positively charged nanopore structure is beneficial. The surface charge on the silica nanoparticles can be manipulated by well known plasma processes.

In some embodiments, the present disclosure provides methods and apparatus to form and use tortuous nanopores to control the translocation speed of molecules so that there is enough time to read a DNA base with high signal to noise ratio and to spread the nanopores out so that the nanopore are optically resolvable in the far field regime (due to the low density of (less than 1/pmt) of nanoscale pores in the partially sealed roof). A readout mechanism is provided, such as using Raman and CARS, to provide label-free molecular recognition mapping or DNS sequencing. A metel-insulator-metal ("MIM") structure is provided that localizes hot spots to monitor the individual bases (moieties) as they translocate the hot spot.

FIGS. 1A-1E depict an exemplary method for fabricating a nanochannel 160 using interferometric lithography and standard semiconductor processing techniques, such as, for example, spin-coating in accordance with various embodiments of the present teachings. There are several advantages for using semiconductor processing, such as, scalability to large area and multilevel processing and integration of nanochannels with other nano/micro/macro components including fluidic, electronic, mechanical, MEMS (micro electromechanical), and optical subsystems or components. The enclosed silica nanochannels fabricated using standard semiconductor processing and interferometric lithography can be potentially useful in photonics, sensory, biological separation, bio-mimic structure, nanofluidics, and catalytic applications.

As shown in FIG. 1A, the method of forming a nanochannel 160 can include depositing a photosensitive film stack 120 over a substrate 110. Non-limiting examples of the substrate 110 can include a pre-cleaned silicon wafer, quartz, and sapphire. In some embodiments, depositing the film stack 120 can include depositing a first layer 125 including an antireflective coating over the substrate 110 and depositing a second layer 126 including a photoresist over the first layer 125. In accordance with various embodiments, the first layer 125 can include a bottom anti-reflective coating (BARC) for i-line photoresist. Yet in other embodiments, the first layer 125 can include a g-line BARC or a deep UV BARC. Non limiting examples of BARC can be XHRiC-16 and Wet-i™ 10-7, manufactured by Brewer Science, Inc. (Rolla, Mo.). In various embodiments, the first layer 125 can be deposited using standard spin coating procedure. In other embodiments, the deposition of the first layer 125 can also include baking the first layer 125 at a temperature from about 100° C. to about 250° C. for about 60 second to about 120 second. The second layer 126 can include at least one of a layer of positive photoresist and a layer of negative photoresist. In certain embodiments, the photoresist can be an i-line photoresist. In other embodiments, the photoresist can be a g-line or a deep UV photoresist. A non limiting exemplary positive photoresist can be SPR510A manufactured by Shipley/Rohm & Haas Electronic Materials (Marlborough, Mass.), and a non limiting exemplary negative photoresist can be NR7-500P, manufactured by Futurrex, Inc. (Franklin, N.J.). The deposition of the second layer 126 including photoresist can also include a baking step to remove residual solvent. In various embodiments, the first layer 125 can have a thickness from about 50 nm to about 200 nm and the second layer 126 can have a thickness from about 200 nm to about 1500 nm.

Figure 1B:
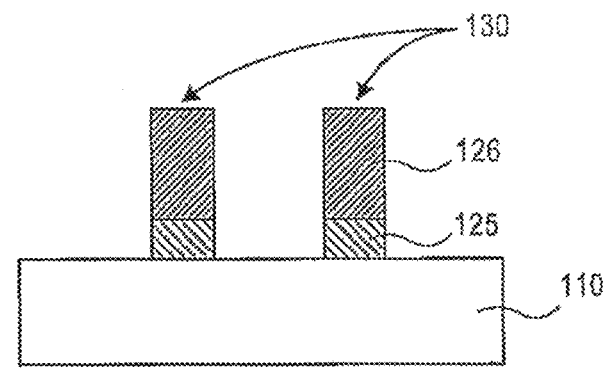

Referring to FIG. 1B, the method of forming a nanochannel 160 can also include forming a pattern 130 on the film stack 120 using lithography. In some embodiments, the pattern 130 can be formed using interferometric lithography. In interferometric lithography, two coherent laser beams with wavelength λ are intersected at an angle 2θ to produce a periodic interference pattern on the film stack 120 with a spatial period $d=\lambda/(2 \sin \theta)$. The angle between the two laser beams can determine the pattern spatial period while the exposure, time, power density, and development time can determine the line width and the pattern morphology. According to various embodiments, a laser in the UV range consistent with the photosensitivity of the film stack 120 can be used to form the periodic interference pattern 130 on the film stack 120, for example, a 248 nm laser can be used for deep UV photoresist and a 355 nm laser can be used for i-line photoresist. Non-limiting examples of a laser in the UV range can include a 355 nm tripled yttrium-aluminum-garnet (YAG) laser, a 248 nm KrF excimer laser, a 193 nm ArF excimer laser, and a 157 nm $F_2$ excimer laser. In various embodiments, using a 355 nm laser, one can form a pattern 130 on the film stack 120 with a spatial period greater than about 200 nm. In other embodiments, an ArF laser can be used to form a pattern 130 on the film stack 120 with a spatial period as small as about 68 nm and with frequency doubling as small as about 34 nm. In some embodiments, the method of forming a pattern 130 on the film stack 120 can include immersion interference lithography. Immersion interference lithography can extend the spatial period of the pattern 130 to $\lambda/2n$, where n is the immersion liquid refractive index. In other embodiments, the method of forming the pattern 130 on the film stack 120 can include conventional lithography either in the ultra-violet (UV) or deep UV region. The step of forming a pattern 130 on the film stack 120 can further include a bake and develop cycle. In some embodiments, the step of forming a pattern 130 on the film stack 120 can further include etching the first layer 125 including an antireflective coating.

Figure 1C:
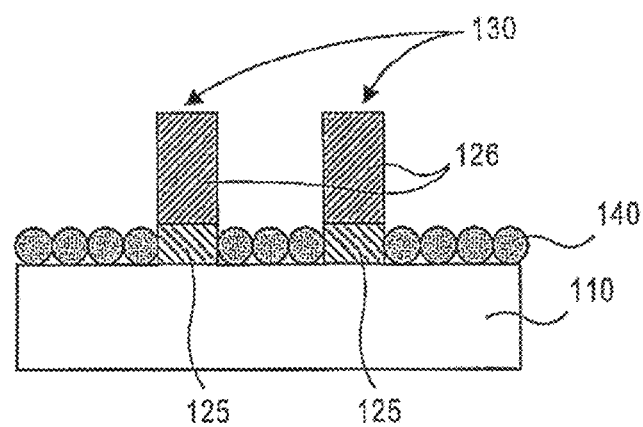
Figure 1D:
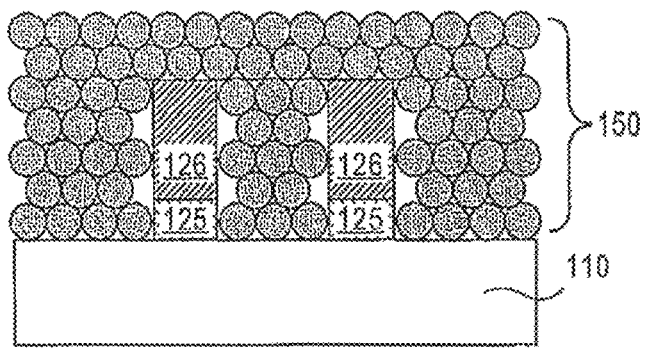

As shown in FIGS. 1C and 1D, the method of forming a nanochannel 160 can include depositing a plurality of silica nanoparticles 140 to form a structure 150 over the pattern 130. In some embodiments, silica nanoparticles 140 can be deposited by spin coating a colloidal dispersion of silica nanoparticles. In other embodiments, silica nanoparticles 140 can be deposited over the pattern 130 using alternative deposition techniques such as, but not limited to, dip coating, convective deposition, and layer by layer electrostatic deposition. In various embodiments, the step of depositing silica nanoparticles 140 can include at least one cycle of spin coating using a suspension of silica nanoparticles. In some embodiments, the step of depositing a plurality of silica nanoparticles 140 can include multiple cycles of spin coating wherein each cycle of spin coating uses a suspension of silica nanoparticles with a same size distribution. In other embodiments, the step of depositing a plurality of silica nanoparticles 140 can include multiple cycles of spin coating wherein at least one cycle of spin coating uses a suspension of silica nanoparticles with a size distribution different than the other cycles of spin coating. While not intending to be bound by any specific theory, it is believed that various cycles of spin coating utilizing suspensions of silica nanoparticles with different size distributions can fill the spaces between the walls of the pattern 130 on the film stack 120 and can also control the thickness of the top sealing layer. For example, in some embodiments, colloidal solutions or suspensions of three different size distributions of silica nanoparticles can be used in three different cycles of spin coating to form the structure 150 over the pattern 130. Exemplary colloidal solutions of silica nanoparticles can include Snowtex® series of colloidal silica: ST-C with a particle size in the range of about 10 nm to about 20 nm, ST-OL with a particle size in the range of about 40 nm to about 50 nm, and ST-ZL with a particle size in the range of about 70 nm to about 100 nm, manufactured by Nissan Chemical America Corporation (Houston, Tex.). The colloidal solutions of silica nanoparticles can be diluted with deionized water to get the desired concentration for spin coating. In some embodiments, colloidal silica nanoparticles can be used in the concentration range of about 1 wt. % to about 10 wt. % and in some cases from about 4 wt. % to about 6 wt. %. In various embodiments, the method of forming a nanochannel 160 can also include agitating the colloidal solution of silica nanoparticles in an ultrasonic bath before spin coating. In some embodiments, the cycle of spin coating can include baking to remove any residual solvent, for example such as baking at a temperature from about 60° C. to about 120° C. for about 1 minute to about 8 minutes.

Figure 1E:
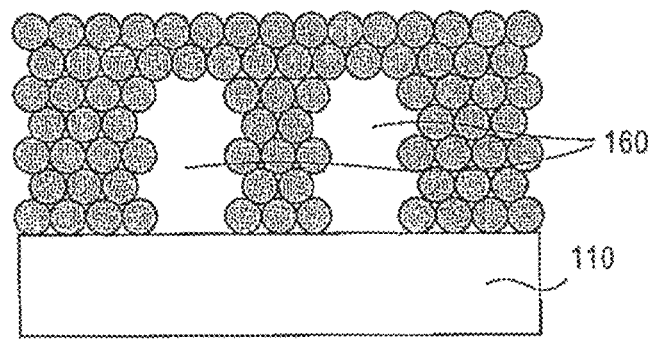

As shown in FIG. 1E, the method of forming a nanochannel 160 can include removing the pattern 130 while retaining the structure 150 formed by the plurality of silica nanoparticles 140. According to various embodiments, removing the pattern 130 can be achieved by calcination. Calcination can be carried out by heating a substance to a high temperature, but below its melting point in the presence of air or controlled environment to bring about thermal decomposition or phase transition in its chemical or physical structure. In some embodiments, the calcination can be carried at about 700° C. to about 900° C. for about 1 hour to about 3 hours and in some cases at about 800° C. for about 1.5 to about 2 hours. In various embodiments, the high temperature calcination can induce some degree of sintering between the silica nanoparticles 140 and thereby enhancing the mechanical stability of the nanochannel structure 150. In other embodiments, the pattern 130 can be removed by techniques such as, but not limited to chemical, plasma, and reactive ion etching. Yet in some other embodiments, piranha composition such 1:1, 1:1.5, and 1:2:30% $H_2O_2$:98% $H_2SO_4$ can be used either alone or in combination with calcination to remove the pattern 130, while retaining the silica nanoparticle structure 150.

Figure 1F:
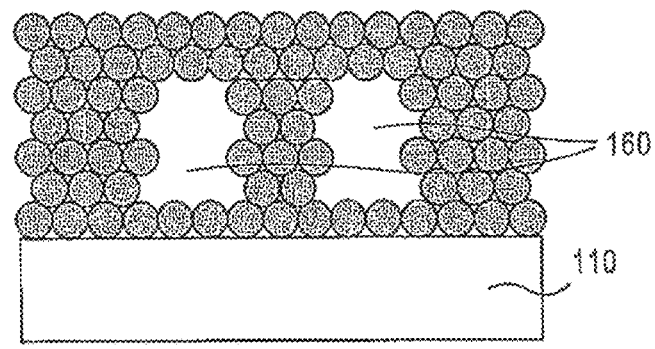
FIGS. 1F and 1G illustrate another embodiment of an exemplary method of forming nanochannels using silica nanoparticles.

According to various embodiments, the method of forming a nanochannel 160 can further include depositing a plurality of silica nanoparticles 140 over the substrate 110 before the step of depositing a photosensitive film stack 120 over the substrate 110, as shown in FIG. 1F.

According to various embodiments, the method of forming a silica nanochannel 160 can further include at least one of increasing the concentration of suspension, adding some bonding agents and increasing the humidity during spin coating to slow the drying process to prevent cracking in the sealing layer. In some embodiments, a bonding agent such as, but not limited to polyvinylpyrrolidone (PVP) can be added to the aqueous colloidal solution of silica and ethylene glycol can be added to the ethanol colloidal solution of silica to prevent cracking in the sealing layer.

In various embodiments, the method of forming a nanochannel 160 can also include modifying the surface of silica nanoparticles 140 to provide additional functionality. In some embodiments, the surface of silica nanoparticles 140 can be modified to provide additional functionality before the step of depositing a plurality of silica nanoparticles 140 to form a structure 150 over the pattern 130, wherein the step of removing the pattern 130 is compatible with the functionalization. In other embodiments, the surface of silica nanoparticles 140 can be modified after the step of removing the pattern 130 while retaining the structure 150 formed by the plurality of silica nanoparticles 140. In some embodiments, the surface of silica nanoparticles can be functionalized to bind biologically active molecules for optical and/or electrical analysis. In other embodiments, a thin layer of gold or silver can be deposited on silica nanoparticles to increase sensitivity of the silica nanoparticles to biomolecules. In various embodiments, the surface of silica nanoparticles can be functionalized for one or more of photonics, catalysis, chemical/biological sensing, separation, biomimic structure, and nanofluidic applications. Furthermore, according to various embodiments, there is a device formed by the exemplary method as shown in FIGS. 1A to 1E including a nanochannel structure, wherein the nanochannel structure includes silica nanoparticles 140 having a functionalized surface for one or more of photonics, catalysis, chemical/biological sensing, separation, bio-mimic structure, and nanofluidic applications.

Figure 1G:
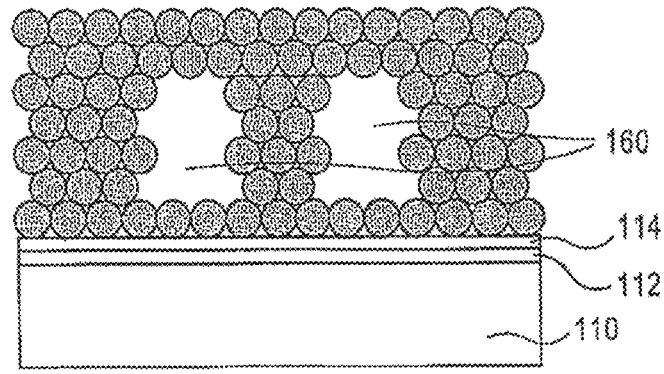

According to various embodiments, the method of forming a nanochannel 160 can further include depositing a releasing layer 112 including chromium over the substrate 110 and under the silica nanoparticles 140, and immersing the structure 150 of silica nanoparticles 140 including nanochannels 160 in a boiling aqueous sulfuric acid solution, thereby releasing the free-standing structure 150 of silica nanoparticles 140 including nanochannels 160. In some embodiments, a support layer 114 to provide mechanical support to the nanochannels 160 can be deposited over the releasing layer 112 as shown in FIG. 1G. In various embodiments, the support layer 114 can comprise silicon nitride. In some other embodiments, the method of forming a nanochannel 160 can further include depositing a support layer 114 over the substrate 110 and under the silica nanoparticles 140, and selectively etching the substrate 110, thereby releasing the free-standing structure 150 of silica nanoparticles 140 including nanochannels 160 on the support layer 114.

According to various embodiments, there is a method of diagnosing the stage of the nanochannel 160 formation. The method can include depositing a drop of a suspension including silica nanoparticles on a patterned surface. The method can also include determining that a nanochannel 160 is not completely formed if the suspension of silica nanoparticles forms an elongated drop along a direction of the pattern 130 due to hydrophobic surface of the silicon substrate 110 and photoresist 125 of pattern 130 and determining that a top of the nanochannel is formed if the suspension of silica nanoparticles shows wetting due to hydrophilic surface of silica nanoparticles 140. For example, upon application of one or more drops of a suspension on the pattern 130 shown in FIGS. 1B and 1C, but before spinning, the suspension of silica nanoparticles can form an elongated drop along the direction of the pattern 130 due to the hydrophobic surface properties of the substrate 110 and the photoresist 126. Once the channel tops are formed as shown in FIG. 1D, partial wetting of the drop of suspension of silica nanoparticles can be observed due to the hydrophilicity of the silica nanoparticles and no contact of the one or more drops of a suspension of silica nanoparticles with the hydrophobic photoresist 126.

Figures 2A, 2B, 2C:
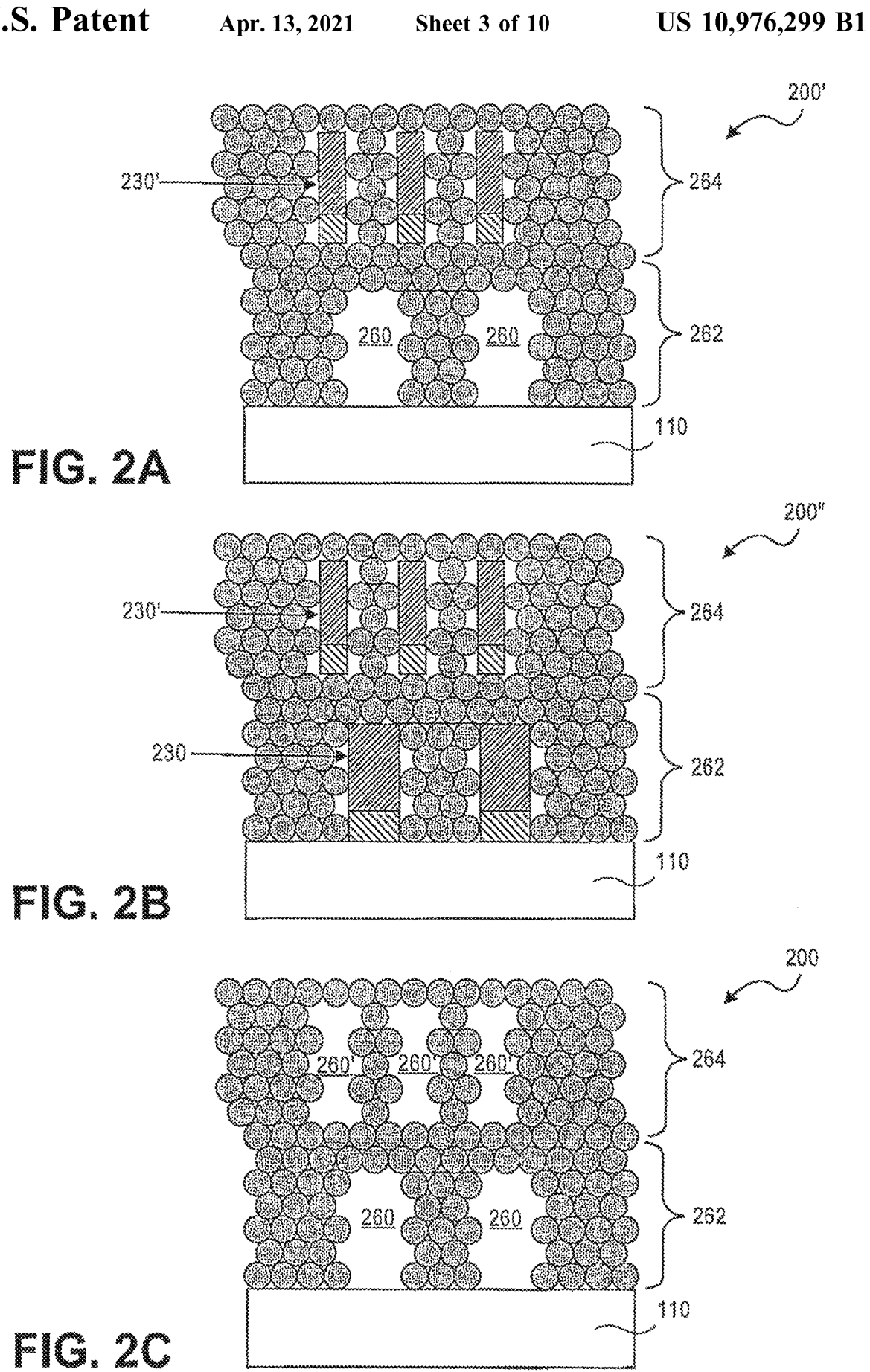
FIGS. 2A-2C illustrates exemplary methods of making multilayer structure of silica nanoparticles.

According to various embodiments, there is a method of forming a multilayer silica nanochannel structure 200 as shown in FIGS. 2A and 2C. The method of forming a multilayer silica nanochannel structure 200 can include forming a first layer 262 of silica nanochannels 260 having a first spatial period and a first aspect ratio. The term "aspect ratio" used herein refers to a ratio of height to width of the silica nanochannels 260. In various embodiments, the method of forming the first layer 262 of silica nanochannels 260 can include: (a) depositing a film stack 120 over a substrate 110; (b) forming a pattern 130 on the film stack 120 using lithography; (c) depositing a plurality of silica nanoparticles 140 to form a structure 150 over the pattern; and (d) removing the pattern 130 while retaining the structure 150 formed by the plurality of silica nanoparticles 140. The structure 150 can include enclosed silica nanochannels 160, as depicted in FIGS. 1E to 1G. The method of forming a multilayer silica nanochannel structure 200 can further include forming a second layer 264 of silica nanochannels 260' having a second spatial period and a second aspect ratio over the first layer 262 of silica nanochannels 260 by repeating the steps a-d employed in forming the first layer 262 of silica nanochannels 260. In various embodiments, the steps a-d can be repeated m−2 times to form an m layered silica nanochannel structure 200. In some embodiments, the first spatial period and the first aspect ratio can be the same as the second spatial period and second aspect ratio. In other embodiments, the first spatial period and the first aspect ratio can be different from the second spatial period and second aspect ratio.

According to various embodiments, there is another exemplary method of forming a multilayer silica nanochannel structure 200 as shown in FIGS. 2B and 2C. The method can include forming a first layer of structure 252 having a first spatial period and a first aspect ratio over the pattern 230 by (a) depositing a film stack 120 over a substrate 110, (b) forming a pattern 130 on the film stack 120 using lithography, (c) depositing a plurality of silica nanoparticles 140 to form a structure 150, 252 over the pattern 130, 230. The method can include repeating the steps a-c to form a second layer of structure 254 having a second spatial period and a second aspect ratio over the first layer of structure 252 as shown in FIG. 2B. The method can further include repeating the steps a-c (m−2) times to get m layered structure 200". The method can further include removing the m layers of pattern 230, 230' while retaining the structure 252, 254 formed by the plurality of silica nanoparticles 140, thereby forming m layered silica nanochannel structure 200. In various embodiments, the first spatial period and the first aspect ratio can be same as the second spatial period and second aspect ratio. In other embodiments, the first spatial period and the first aspect ratio can be different from the second spatial period and second aspect ratio.

Figure 3:
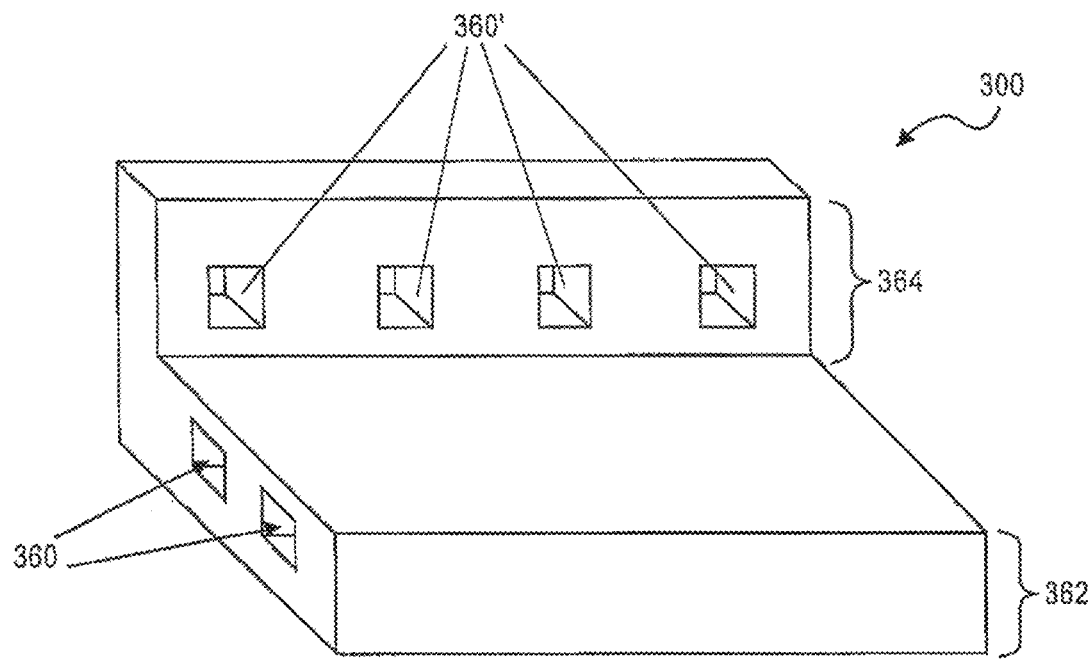
FIG. 3 is a schematic illustration of an exemplary perpendicular layered nanochannel structure.

According to various embodiments, the method of forming a multilayer silica nanochannel structure 200 can further include rotating the substrate 110 to a desired angle during the formation of a $m^{th}$ layer of silica nanochannels to form the $m^{th}$ layer at the desired angle relative to the $(m-1)^{th}$ layer. In some embodiments, the layers can be at an angle in the range of about 0° to about 90°. FIG. 3 is a schematic illustration of an exemplary substantially perpendicular layered nanochannel structure 300 wherein a plurality of nanochannels 360 in a first layer 362 with a first spatial period and first aspect ratio are perpendicular to a plurality of nanochannels 360' in the second layer 364 with a second spatial period and a second aspect ratio. In some embodiments, the first spatial period and the first aspect ratio can be same as the second spatial period and the second aspect ratio. In other embodiments, the first spatial period and the first aspect ratio can be different from the second spatial period and the second aspect ratio.

Figure 4:
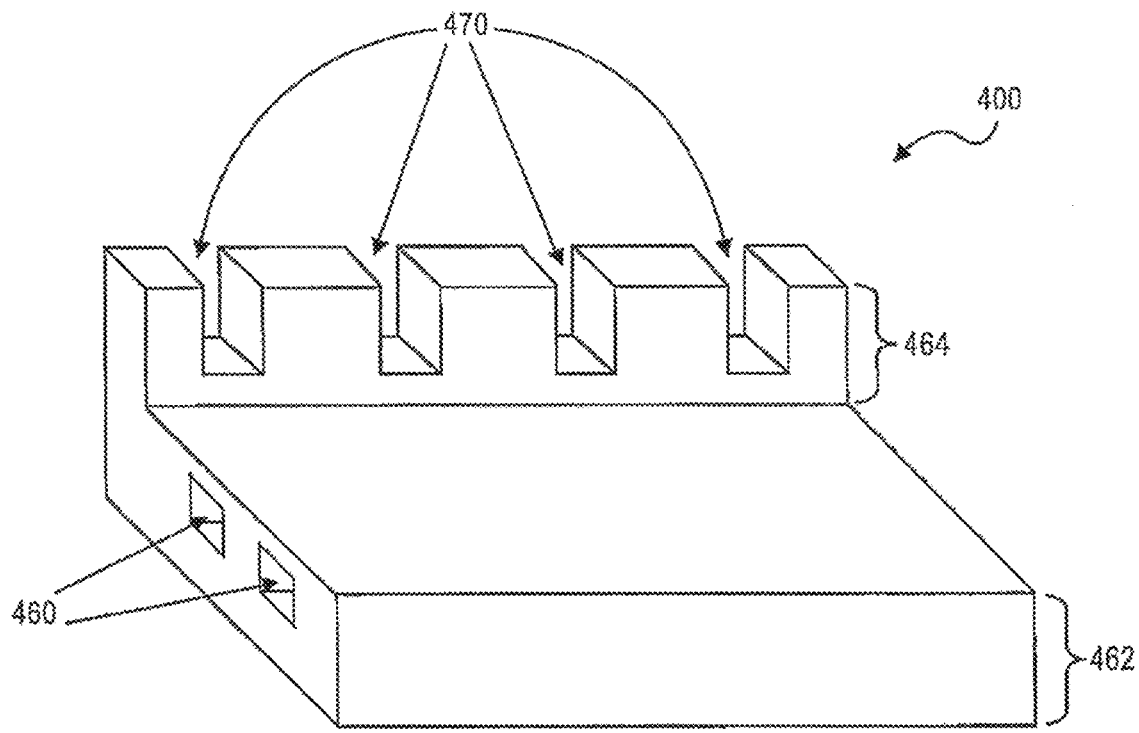
FIG. 4 illustrates another exemplary multilayer nanochannel structure according to various embodiments of the present teachings.

FIG. 4 illustrates another exemplary multilayer nanochannel structure 400 according to various embodiments of the present teachings. The multilayer nanochannel structure 400 can include at least one layer 462 including at least one enclosed silica nanochannel 460 and at least one layer 464 including at least one open silica nanochannel 470. In some embodiments, the multilayer silica nanochannel structure can include hybrid enclosed structures such as one dimensional channels and two dimensional cavities in other layers, as disclosed in D. Xia, S. R. J. Brueck, Nano Letters, 2004, Vol. 4, No. 7, 1295, which is incorporated by reference herein in its entirety.

According to various embodiments, there is porosity between the nanochannels 160 and between different layers 262, 264. The porosity of the nanochannel structure 200, 300, 400 can be of the scale of d/3, where d is the diameter of the silica nanoparticles and can be controlled with the size of the silica nanoparticles. A porous sidewall 562 including a plurality of pores 595 between nanochannels 560 and 560' is shown in FIG. 5.

Figure 5:
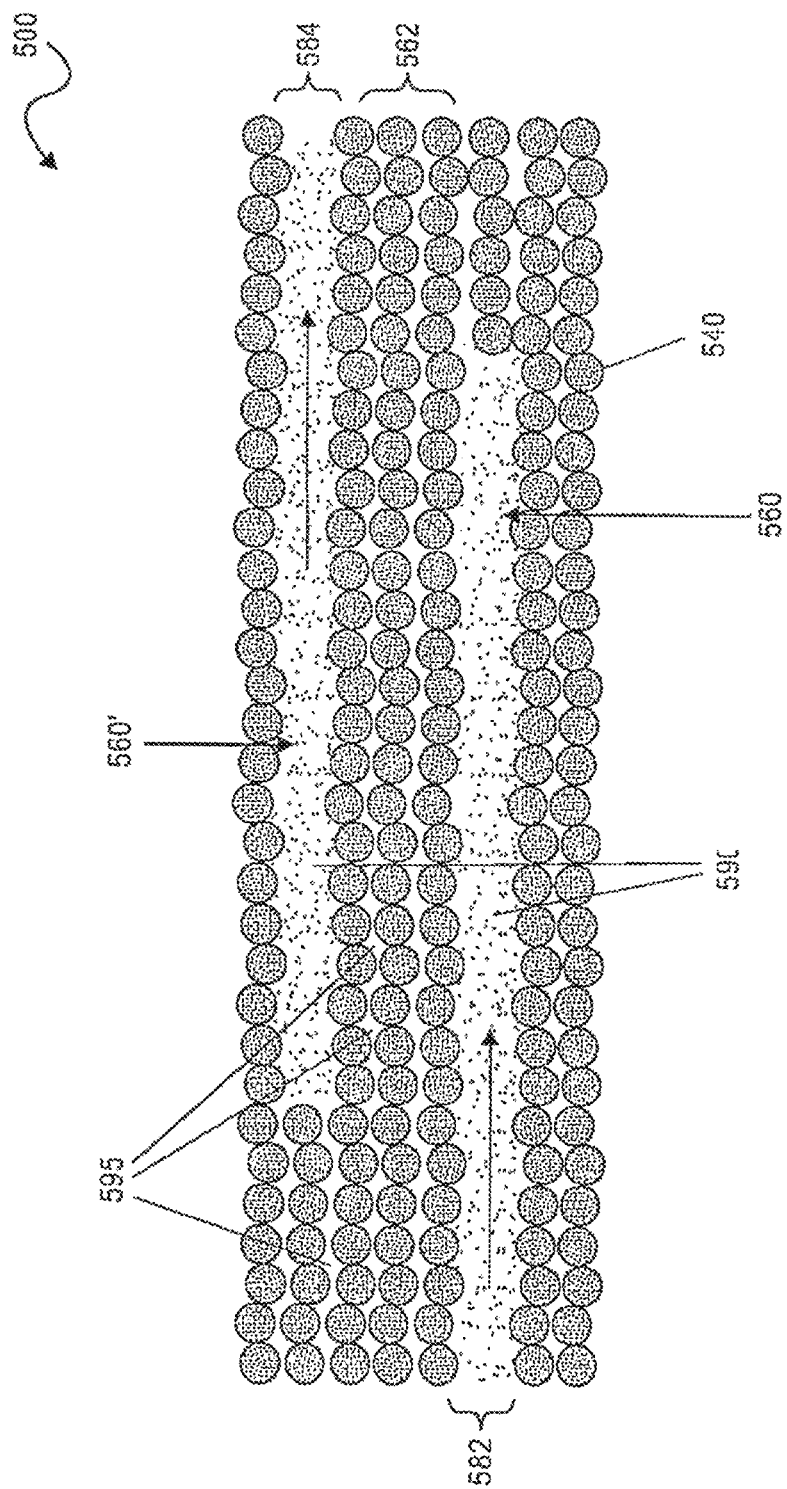
FIG. 5 depicts an exemplary nanochannel device for selectively separating components of a fluid in accordance with the present teachings.

FIG. 5 depicts an exemplary nanochannel device 500 for selectively separating components of a fluid 590. The exemplay nanochannel device 500 includes at least one first nanochannel 560 with a first opening 582 and at least one second nanochannel 560' with a second opening 584, wherein the first opening 582 is in a direction different from the first opening 584. The exemplary nanochannel device 500 can further include at least one porous sidewall 562 having a plurality of pores 595 between the first 560 and the second 560' nanochannel, wherein the first nanochannel 560, the second nanochannel 560', and the at least one porous sidewall 562 are disposed such that the fluid 590 enters through the first opening 582 opening of the first nanochannel 560, percolates through the plurality of pores 595 of the porous sidewall 562 and exits through the second opening 584 of the second nanochannel 560'. In various embodiments, the silica nanoparticles 540 can be functionalized to selectively transport one component of the fluid 590.

According to various embodiments, the method of forming silica nanochannel 160 and silica nanochannel structure 200 can have numerous degrees of freedom. In some embodiments, the spatial period, shape, and size of the nanochannels 160 can be controlled by varying the lithographic parameters such as thickness and photoresist type (i.e. positive or negative photoresist), exposure, development times, and develop parameters (such as postbake time and temperature, developer concentration, temperature and time). In other embodiments, the silica nanochannel 160 profile can be controlled by controlling the spin coating process (spin program and the number of deposition cycle), concentration of colloidal silica nanoparticles and silica nanoparticle size.

Figure 6B:
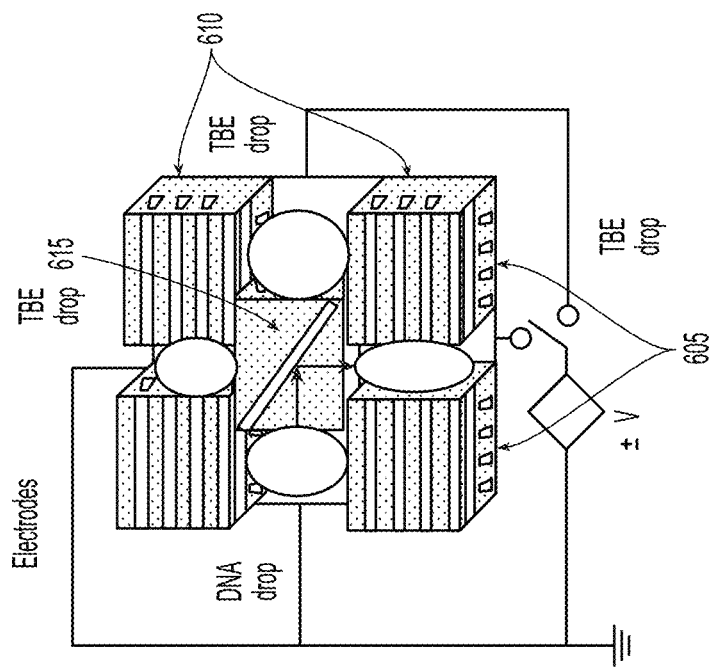
FIGS. 6A and 6B depict another exemplary nanochannel device for selectively separating components of a fluid in accordance with the present teachings.
Figure 6A:
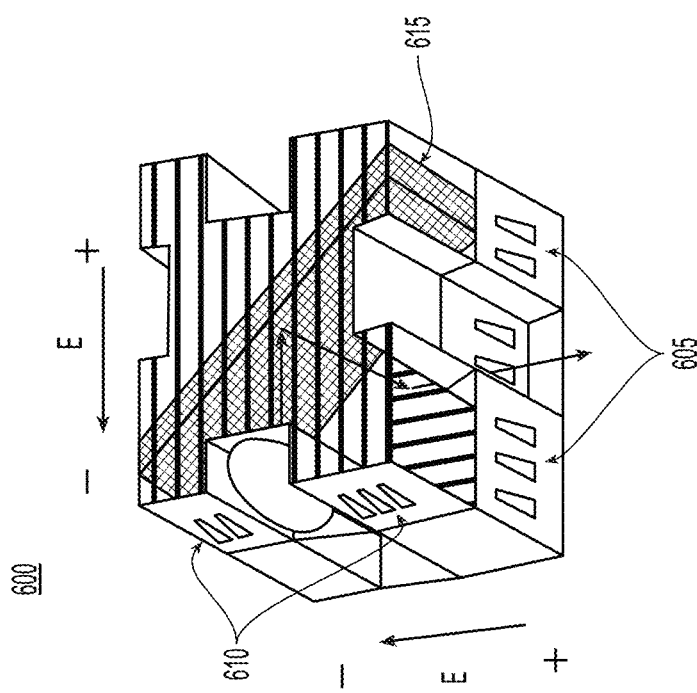

FIGS. 6A and 6B depict an exemplary nanochannel device 600, similar to that depicted in FIG. 5, for selectively separating components of a fluid 690. Nanochannel device 600 is shown as a two level chip with cross channels and a porous layer functioning as a separation media, which can function to filter and collect separated molecules. A first layer of silica nanochannels 605 is first formed using the processes described above. A second layer of silica nanochannels 610 is then formed on top of the silica nanoparticles such that the nanochannel array in the second layer is arranged perpendicular to the nanochannel array in the first layer. The calcination step to remove the photoresist material can be performed once for each layer, or reserved until both layers of nanochannels are formed. For example, each of the nanochannels in the first and the second layer can be about 500-nm wide. One or more silica nanoparticle barriers are formed within the second layer of silica nanochannels. As shown in FIG. 6A, a silica nanoparticle barrier 615 can provide a zone for biological molecules (e.g., DNA) to accumulate. Controlling the thickness of the roof of the first layer of nanochannels 605 relative to the width of the barrier or barriers 615 provides a means of adjusting the separation processes. The biological molecules can then move through the top channels accumulate along the barrier and penetrate through the porous roof into the bottom layer and move in a perpendicular direction. A buffer solution can be added to provide conductivity. An applied electric field to the wells can drive DNA in the top channels and provide fast accumulation at the barrier. The applied electric field can then be applied between the top and bottom layers of nanochannels to drive molecules across the porous roof. Molecules that penetrate into the first layer can be removed from the channels by an electric field applied to the pair of wells in the bottom layer, as shown in FIG. 6B. Controlling the field strength and the length of time it is applied provides further degrees of freedom in adjusting the separation processes.

Figure 7C:
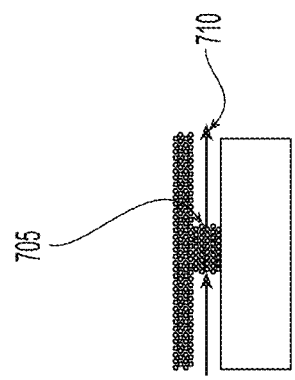
FIGS. 7A to 7F depict another exemplary nanochannel device 700 for selectively separating components of a fluid in accordance with the present teachings.
Figure 7B:
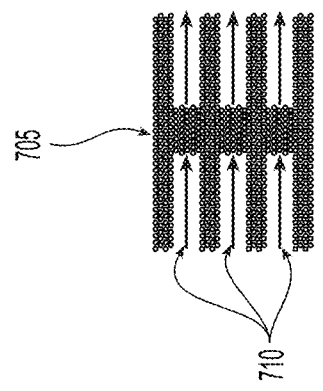
Figure 7A:
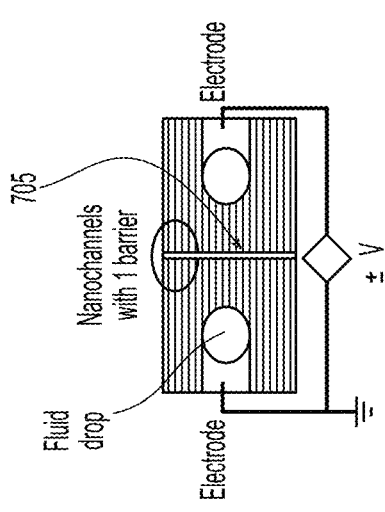
Figure 7F:
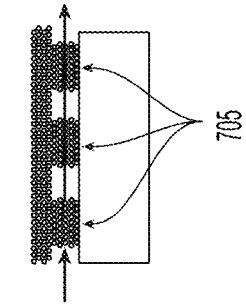
Figure 7E:
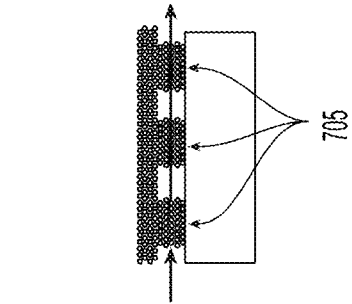
Figure 7D:
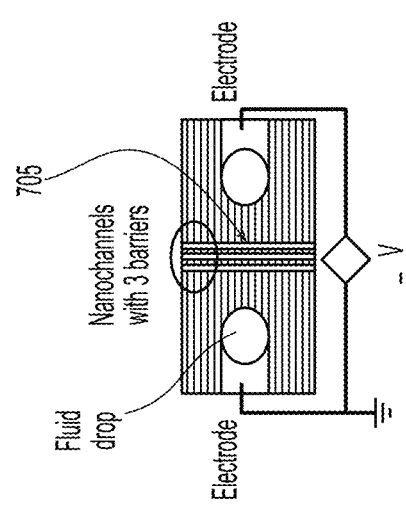

FIGS. 7A-7F depict an exemplary nanochannel device 700, similar to that depicted in FIG. 5, for selectively separating components of a fluid 790 with the difference being that in FIG. 5 the nanochannels are parallel and separated by a long porous barrier. Adjacent nanochannels need to be opened/closed at the two ends with is difficult since the channels can be closer than typical lithographic resolutions. This is avoided in FIG. 7 by having the nanochannels aligned and separated by a narrow barrier region. Nanochannel device 700 (with one barrier) and 750 (with three barriers) comprises nanochannels 710 and one or more barriers 705 from nanoparticles manufactured perpendicular to the channels. The one or more barriers 705 can be fabricated by additional illumination of photoresist patterns after interferometric lithography on a mask aligner before development of the photoresist and spinning of the silica nanoparticles. The one or more barriers 705 can be relatively thin, for example, about 3 µm in thickness, limited only by the size of the nanoparticles and the available lithography. However, this is merely one example of barrier thickness and other suitable thicknesses can also be used. A chip with a barrier (3 µm) is shown in FIG. 7A, enlarged area of interest is shown in FIG. 7B from the top and in FIG. 7C from the side. It is also possible to make several barriers for different types of filtration. A chip with three barriers perpendicular to the channels is shown in FIG. 7D, enlarged area of interest is shown in FIG. 7E from the top and in FIG. 7F from the side.

For example nanochannel devices 700 and 750 can be fabricated using the techniques discussed above. In particular, a photosensitive film stack can be deposited over a substrate. A first pattern can be formed on the film stack using interferometric lithography. This film stack is developed and nanoparticles are deposited by spin coating to form an array of nanochannels. A second pattern can be formed on a second film stack deposited over the first layer of nanochannels using interferometric lithography and a mask aligner to form one or more barriers in the nanochannel. A plurality of silica nanoparticles can be deposited to form the second layer of nanochannels which incorporates the one or more barriers. Finally, the first pattern and the second pattern can be removed, for example by heating in an oxygen ambient, while retaining the structure formed by the plurality of silica nanoparticles, wherein the structure comprises an enclosed nanochannel with the one or more barriers formed along a portion of the enclosed nanochannels.

Figure 8:
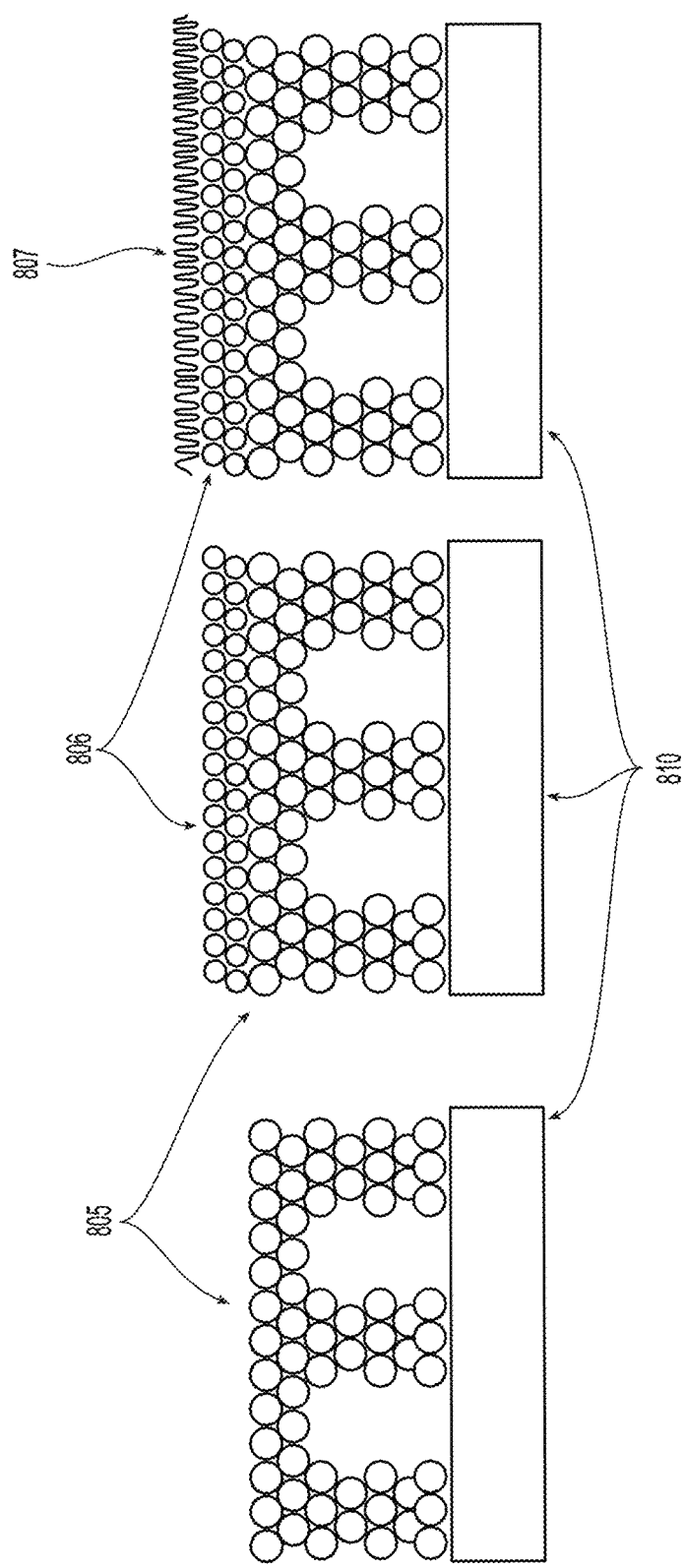
FIG. 8 illustrates an exemplary method of forming nanochannels using silica nanoparticles in accordance with various embodiments of the present teachings.

Evaporation through the roof of the nanochannels into the ambient above the chip limits the duration of an experiment due to drying of the fluid. Additionally, under an applied electric field, the fluid can transport through the roof instead of the barriers and bead up on the top surface of the roof. It is desirable to provide a sealant for the roof while still allowing diffusion of the liquid and biological moieties through the porous walls. Since the roof and walls are porous, this requires line-of-sight deposition technique such that the deposition is self-sealing on the top few layers of the roof and does not penetrate into channel regions, leaving the porosity of the barriers and the channel walls. Chemical vapor deposition (CVD) of a film 806 over the roof significantly decreases the evaporation through the roof. Both $Si_3N_4$ and $SiO_2$ films have been used successfully as shown schematically in FIG. 8. An additional atomic layer deposition (ALD) step 807 following the CVD step provides additional sealing. It is important to block the openings into the nanochannel areas during this ALD step to avoid ALD sealing of the barriers and channel walls. Among other materials, $Al_2O_3$ can be used for this atomic layer deposition step.

Following examples set forth below illustrate different degrees of freedom that can be utilized in practicing the present teachings. It will be apparent to one of ordinary skill in the art, however, that the present teachings can be practiced with many other sets of parameters in accordance with the disclosure.

Example 1—Preparation of Enclosed Silica Nanochannels

Enclosed silica nanochannels with a height of about 300 nm and a width of about 120 nm on a about 1 cm long substrate were obtained using silica nanoparticles with diameter in the range of about 40 nm to about 50 nm. Interferometric lithography with a 355 nm tripled yttrium-aluminum-garnet (YAG) laser was used to produce the periodic pattern. Snowtex® series of colloidal silica, ST-OL was used in six cycles of spin coating and calcination at about 800° C. was done for about 2 hours. The thickness of the sealing layer was in the range of about 100 nm to about 150 nm (i.e. 2-3 particles).

Example 2—Preparation of High Aspect Ratio Silica Nanochannels

High aspect-ratio silica nanoparticle walls in the range of about 2:1 to about 4:1 and thin top seals (with one to two silica nanoparticles) were obtained using a thick coat of negative photoresist (NR7-500P from Futurrex, Inc.). The thickness of the negative photoresist was in the range of about 500 nm. Silica nanoparticles with a diameter of about 50 nm were used to form high aspect ratio nanochannels with a spatial period of about 500 nm and about 1000 nm. Silica nanochannels with a spatial period of about 1000 nm were obtained using silica nanoparticles having a diameter of about 80 nm. Furthermore. silica nanochannels with spatial period of about 500 nm were obtained with silica nanoparticles having a diameter of about 15 nm.

Example 3—Preparation of Two Layered Silica Nanochannel Structures

Two layer silica nanochannel structures were fabricated using silica nanoparticles having a diameter of about 50 nm, through repeat processing on a single substrate. After a first layer of buried silica nanochannels was fabricated, the full process, including application of antireflective coating and photoresist films, interferometric lithographic pattern definition and development, spin coating of silica nanoparticles, and calcination led to formation of a second layer of enclosed nanochannels over the first layer. In one case, the silica nanochannels in the first layer were parallel to the second layer with both layers having a spatial period of about 500 nm. In another case, the silica nanochannels in the first layer with a spatial period of about 1000 nm were perpendicular to the second layer with spatial period of about 500 nm.

According to various embodiments, there is a device including at least one of a single layer, multi layer, and a combination of single and multi layer nanochannel structure, wherein the nanochannel structure can include silica nanoparticles with a functionalized surface to bind biological molecules for optical and/or electrical analysis. In some embodiments, the surface of silica nanoparticles can be functionalized for at least one of photonics, catalysis, chemical/biological sensing, separation, bio-mimic structure, and nanofluidic applications.

According to some embodiments, the nanoparticles form both the sidewalls and the roofs of the nanochannels, with the nanoparticles in the roof forming tortuous nanopores, which, should a sample including long-chain molecules to be analyzed be placed in the nanochannels, the long-chain molecules would have to traverse the pores in order to reach the roof and vice versa. According to some embodiments, 50-nm-diameter silica nanoparticles are used, but both the size and the material structure are flexible. Capillary forces during deposition force the nanoparticles (NP) into a hexagonal close-packed geometry. As a rough estimate, this means that the spaces between nanoparticles are ~NP diameter/3 or ~17 nm. The pores are complex, 3D paths, similar to the spacings and open paths created when oranges are piled up in the local supermarket. However, it should be understood that the actual structure is highly complex due to the significant dispersion in nanoparticle sizes which is under the control of the nanochannel fabricator. For the purposes of the present disclosure, we refer to the spacings and open paths created by the nanoparticles as "tortuous nanopores." In layer-by-layer deposition, steric effects due to the NP size dispersion will create a range of nanopore sizes. By way of example, the roof can be about several nanoparticles in thickness, where each nanoparticle can be about 50 nm in diameter, resulting in a total roof thickness of at least 100 nm in thickness.

It will be appreciated that some applications that utilize the above-described nanochannels would benefit from the ability to specifically control the density of the nanopores in the nanochannel roof. For example, it might be desirable to reduce the density of the nanopores, so as to reduce or eliminate unwanted leakage or transport of samples through the roof and/or enabling the translocation, transportation, or identification of specific long chain molecules of interest including, for example, single stranded DNA (ssDNA), RNA and proteins. Accordingly, the present disclosure provides for the formation of tortuous nanopores that are formed in the nanochannel roof and which can be further decreased in size and density by standard film deposition processes such as e-beam evaporation, sputtering, CVD and/or conformal atomic layer deposition (ALD). (The film deposition both closes some of the pores, reducing the density, and also decreases the sizes of the remaining pores allowing only a single long chain molecule to transit at a time.) The ALD process further constricts the apertures along the pores on the order of about 1 nm.

According to various embodiments, after the tortuous nanopores are self-assembled in the roof, the roof is partially sealed, by which it is meant that some, but not all, of the externally accessible pores formed by the self-assembly and calcination of the nanoparticles are sealed. The accessible pores are either sealed or unsealed (which also includes pores that are partially sealed). The partially sealed roof comprises no more than one unsealed nanochannel per squared micron.

According to various embodiments, the pores may be sealed using either CVD, ALD, or a combination of both. For example, as described in greater detail below, a combination of CVD and ALD can be used to close the smallest pores to prevent leakage or penetration of the sample through the roof, control pore density, and ensure compatibility with optical resolution.

According to various embodiments, a nanopore structure with at least one manufactured nanopore can be assembled on the roof of the tortuous nanopore structure. This could be a dense nanopore structure such as a graphene sheet or a sparse nanopore structure such as a nitride film in which nanopores are fabricated, e.g. by ion-milling, either before or after application of the film to the tortuous nanopore structure. Since the goal is the read of long-DNA (as well as RNA and proteins) molecules, up to ~50,000 bases or ~10 µm of natural length, the tortuous nanopores structure reduces the DNA translocation speed through the conventional registering nanopore.

An alternative embodiment is to apply the tortuous nanopore to an existing nanopore structure, for example an ion- or electron-milled pore in a nitride film. This could be done by applying a nanoparticle suspension to one side of the pore and allowing it to dry to form the tortuous pathway for the DNA or similar long-chain molecule. The existing nanopore diameter can be adjusted so that ALD can be used both to restrict the translocation through the tortuous pathway through the nanoparticles and to decrease the diameter of the nanopore in the film. The pore in the film can be fabricated either before or after the formation of the tortuous pathway.

In addition to adjusting the nanopore density and pore size, the addition of a non-porous secondary optically transparent roof in close proximity to the porous roof provides a means to adjust the local humidity and hence control the evaporation rate out of the nanochannels. This roof can provide multiple enhancements to the device: 1) it can provide a micro- or macro-flow channel for the buffer/molecular solution on exiting the nanopores to allow removing them from the region of the pore and controlling the local humidity at the nanopore; 2) it can provide an optical quality surface for far-field optical measurements; and 3) with the addition of a transparent electrode such as ITO, or a gridded electrode structure, it can allow for further manipulation of the quasi-static electric fields in the vicinity of the tortuous nanopore to control the translocation velocity.

A metal-insulator-metal (MIM) structure can be deposited by a combination of anisotropic and isotropic deposition processes and can be self-aligned to the nanopores. For example, a thin metal film can first be deposited by e-beam evaporation or sputtering, a directional process that will not close the nanopore. Then a thin (e.g., ~0.3 to 1 nm) insulator film can be deposited by atomic layer deposition, a conformal deposition process that will further reduce the nanopore diameter. Finally, a second metal film can be deposited by a directional process. This provides a self-aligned, massively parallel nanofabrication technology that bypasses the need for any high-resolution, ~1-nm lithography and allows far-field optical recording of near-field processes with the necessary resolution. The MIM structure both provides strongly enhanced electromagnetic fields, allowing single molecule detection, and the near-field nanoscale resolution necessary to resolve individual bases in, for example, single-strand DNA (ssDNA) where the individual base dimensions are roughly 0.3 nm cubes. According to various embodiments, the motion of the sample through the nanochannels and nanopores is slowed by the tortuosity of the nanopores and can be further controlled by voltages applied to the channels, the MIM, and to control electrodes, which could be placed, for example, above the nanochannel roof.

The above-described technique can thus be used to form Raman "hot-spots" in those embodiments where a Raman spectroscopy-based detection method is used. Surface Enhanced Raman Scattering (SERS) and surface-enhanced coherent anti-Stokes Raman scattering (SECARS) are related techniques that offer the potential for both enhanced signal levels that have already demonstrated single molecule level sensitivities. Both techniques rely on localized "hot-spots," often at the interstices between metallic particles (for example in colloidal aggregates). These hot-spots serve two essential purposes: 1) to ensure large electromagnetic fields (SERS, a two-photon process, scales as $\sim E^4$ and SECARS, a four-wave mixing process, as $\sim E^8$) providing the single molecule sensitivity and 2) to localize the interaction volume to single-base level dimensions—many orders-of-magnitude smaller than $\lambda^3$—providing the necessary single base resolution. This separation can be engineered by the MIM structure described above. Thus, field enhancements of 30, which are quite reasonable for nanostructure metals, lead to Raman enhancements of $\sim 10^6$ and to SECARS enhancements of $10^{12}$. Simply stated, Raman scattering is a mixing between an incident photon at frequency $\omega_1$ and a molecular vibration at frequency v, to provide an anti-Stokes signal at $\omega_1+v$ and a Stokes signal at $\omega_1-v$. The intensity, of the anti-Stokes signal is proportional to the occupation number of the molecular vibration, and is generally small at room temperature where $\kappa T \leq v$, where $\kappa$ is Boltzman's constant and T the absolute temperature (Kelvin). Coherently driving the excitation using two coherent sources at frequencies $\omega_1$ and $\omega_1-v$ and detecting the signal at $\omega_1+v$ provides another enhancement of the Raman signal. This is known as coherent anti-Stokes Raman scattering or CARS. By using a broadband second (lower) laser frequency (for example a supercontinuum), we can probe all four bases simultaneously. CARS is a four-wave mixing process (described by a third order nonlinear susceptibility, $\chi^{(3)}$). An alternate approach is to provide a source of phonons that directly excite the vibrational mode. These techniques maybe preferred in some cases as they are label-free and do not require any manipulation of the unknown DNA before sequencing. Raman spectra of each of the four DNA bases are well known, and offer readily separable signatures. Fluorescence labeling techniques have been demonstrated and may be used as an alternate sequencing approach. Fluorescence, as spontaneous Raman scattering (SERS), involves two photons, and is enhanced ($E^4$) and localized by plasmonic effects; however it is a much stronger optical signal than Raman scattering and so is more easily detected.

Figure 9:
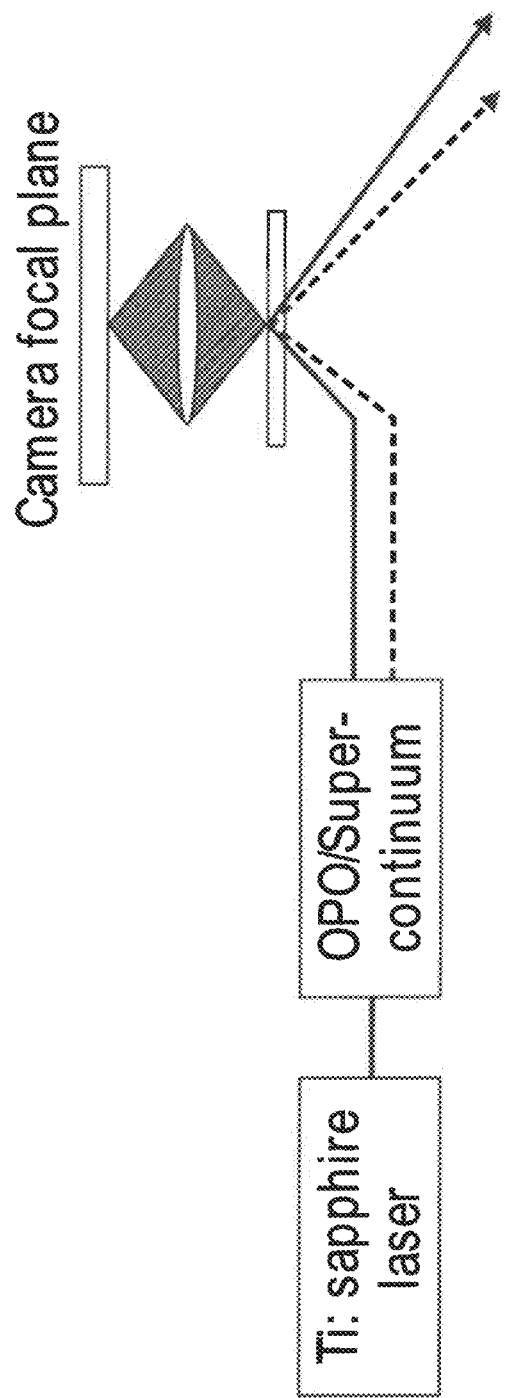
FIG. 9 shows an example schematic optical scheme according to embodiments.

A schematic optical scheme is shown in FIG. 9. According to an embodiment, the pump and Stokes excitation beams can be generated with a Ti:sapphire laser and a nonlinear process such as an optical parametric oscillator or a supercontinuum generation scheme. The advantage of the supercontinuum is that all four bases can be probed simultaneously (using, for example, dielectric filters to separate the anti-Stokes wavelengths). According to an exemplary arrangement, the laser illumination is from the bottom of the nanochannel substrate, so that most of the pump light is reflected by the MIM structure, simplifying the isolation of the SECARS signals. Since the device is probing a set of single bases, each localized to a resolution much smaller than the optical wavelength, there is no phase-matching requirement as in traditional CARS, and the radiation is emitted in a dipole radiation pattern. A judicious choice of the illumination and collection geometries suppresses the non-resonant four-wave mixing signal from the substrate and nanochannel materials, enhancing the desired SECARS detectivity. According to an embodiment, the SECARS signal can be collected with a high-NA objective and imaging onto either a single detector for photon counting or onto a high-sensitivity camera(s) for massively parallel multi-pore analysis. Since, by design, the pores are separated by more than the resolution limit of the objective, the measurements for each channel are optically independent.

According to various embodiments, it is generally desirable for the Raman hot-spot to be sufficiently small and aligned with the exit of the tortuous nanopore so that the bases transit sequentially through the hot-spot. The presently described technique takes advantage of a self-aligned fabrication technique to ensure this overlap. Deposition processes such as e-beam evaporation and sputtering are directional, so that when applied to the rough surface of our ALD coated nanoparticle roof; holes will form in a deposited metal film just at the pore locations, serving to define the locations of the hot spots. Additional localization can be enforced by fabricating a MIM structure. This can be done using ALD to sequentially deposit a very thin dielectric layer (e.g., ~0.5 to 1 nm) on the metal followed by a second metal layer, either with ALD or with directional deposition. The highly nonlinear SECARS process further reduces the extent of the hot-spot, providing the required single base resolution. As a result of the stochastic distribution of pore sizes, there might be some pores that allow translocation of more than one molecule, for example more than one ssDNA strand simultaneously, or of residual dsDNA strands. Fortunately, these can be detected with temporal coincidences of reads of two bases in the same location, and these pores can be ignored computationally, without requiring any hardware modifications.

According to various embodiments, SECARS enables nanoscale-level discrimination, even between bases in ssDNA. While the interaction leading to the Raman signature is confined in the near-field by the small dimensions of the apertures in the MIM and the spacing between the two metal films, the readout is in the far-field providing a massively parallel readout where each camera pixel can independently and simultaneously address individual nanopores. In a fully engineered system, long reads (>50 kilo-bases) with up to one million nanopores, separated by more than the resolution element of the observation microscopy, and a camera operating at 30 frames/s giving a throughput of as much as $10^{11}$ bases per hour is possible. Furthermore, the fluidic chip can be inexpensively produced and is designed to be field replaceable.

As stated above, according to some embodiments, the presently disclosed apparatus can be used for the rapid and inexpensive separation, transportation, detection, and/or sequencing (referred to herein collectively as "manipulation") of nucleic acids, including, for example, genomic DNA. According to this embodiment, each nanopore in the roof structure becomes an independent DNA translocation site; multiple such sites can be optically resolved in parallel (~1M per mm$^2$). Moreover, it will be understood that a variety of potentials could be applied across the device to control the DNA translocation. For example, as described in greater detail below, three or more potentials could be applied: along the nanochannels; between the nanochannels and the plasmonic readout structure; and above the plasmonic readout structure to provide exquisite control of the DNA translocation.

FIGS. 10A-10B depict of an exemplary method of DNA manipulation according to an embodiment of the disclosure. The DNA enters the nanochannel from the reservoir (not shown) on the left and is uncoiled by the constraints of the nanochannel. Three sizes of silica nanoparticles (grey-scale differentiated) are shown to represent the dispersion in NP size. The NPs form a close-packed quasi-hexagonal lattice disturbed by steric effects as a result of the size dispersion, giving rise to a non-uniform set of tortuous pathways through the roof. An ALD process, represented by the dark borders on the NPs, closes the bulk of the nanopores (as evidenced by the dramatic reduction in evaporation rate through the roof following the ALD treatment), resulting in a density of remaining nanopores that is compatible with far-field optical resolution. The ALD can be controlled so that the majority of the remaining tortuous nanopores are sufficiently small that only a single ssDNA strand can pass through at a time. Finally, a metal-insulator-metal (MIM) structure (in expanded view in FIG. 10B) localizes the enhanced electromagnetic fields and provides single base measurement capability.

While the invention has been illustrated with respect to one or more implementations, alterations and/or modifications can be made to the illustrated examples without departing from the spirit and scope of the appended claims. In addition, while a particular feature of the invention may have been disclosed with respect to only one of several implementations, such feature may be combined with one or more other features of the other implementations as may be desired and advantageous for any given or particular function. Furthermore, to the extent that the terms "including", "includes", "having", "has", "with", or variants thereof are used in either the detailed description and the claims, such terms are intended to be inclusive in a manner similar to the term "comprising."

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A nanochannel device for manipulating a target long chain molecule comprising:
   a first plurality of nanochannels, wherein each nanochannel comprises a first opening and a second opening of the first plurality of nanochannels;
   a second plurality of nanochannels, wherein each nanochannel comprises a first opening and a second opening of the second plurality of nanochannels, wherein the first plurality of nanochannels, the second plurality of nanochannels, or both are self-assembled and formed by direct spin-coating of a plurality of nanoparticles over a sacrificial polymer structure on a substrate; and
   a barrier positioned between the first plurality of nanochannels and the second plurality of nanochannels, wherein the barrier comprises a plurality of silica nanoparticles, wherein the barrier allows the target long chain molecule to accumulate.

2. The nanochannel device of claim 1, wherein the second plurality of nanochannels are arranged perpendicular to the first plurality of nanochannels and separated from the first plurality of nanochannels by the barrier.

3. The nanochannel device of claim 1, wherein a thickness and/or a pore size of the barrier is controlled by a size of the nanoparticle to affect a flow of moieties across the barrier.

4. The nanochannel device of claim 1, further comprising functionalized silica nanoparticles to selectively control a translocation speed of the target long chain molecule through a tortuous nanopore.

5. The nanochannel device of claim 1, wherein the target long chain molecule comprises a biological molecule, DNA, RNA, or a protein.

6. The nanochannel device of claim 1, wherein the first plurality of nanochannels, the second plurality of nanochannels, or both have a period of about 1 μm and a linewidth of about 10 nm to about 100 nm.

7. The nanochannel device of claim 1, wherein the plurality of nanoparticles form tortuous nanopores that slow a translocation speed of the target long chain molecule.

8. The nanochannel device of claim 1, wherein the plurality of nanoparticles are deposited in a quasi-hexagonal-close-packed geometry.

9. The nanochannel device of claim 1, wherein a roof structure of a portion of the first plurality of nanochannels, a portion of the second plurality of nanochannels, or both are sealed.

10. The nanochannel device of claim of claim 9, further comprising a chemical vapor deposition (CVD) film over a top surface of the roof structure.

11. The nanochannel device of claim 10, wherein the CVD film comprises $SiO_2$, $Si_3N_4$, or both.

12. The nanochannel device of claim 1, wherein the barrier allows fluids to enter a first opening of a first nanochannel of the first plurality of nanochannels and exit a first opening of a second nanochannel of the second plurality of nanochannels.

* * * * *